(12) United States Patent
Fang et al.

(10) Patent No.: US 6,638,232 B1
(45) Date of Patent: *Oct. 28, 2003

(54) SYSTEM AND METHOD FOR DETECTING AND LOCATING HEART DISEASE

(76) Inventors: Dan Qun Fang, P.O. Box 6787, Rosemead, CA (US) 91770; Hai Xiang Liu, P.O. Box 6787, Rosemead, CA (US) 91770

(*) Notice: Subject to any disclaimer, the term of this patent is extended or adjusted under 35 U.S.C. 154(b) by 199 days.

This patent is subject to a terminal disclaimer.

(21) Appl. No.: 09/712,702

(22) Filed: Nov. 13, 2000

Related U.S. Application Data

(63) Continuation of application No. 09/035,476, filed on Mar. 5, 1998, now Pat. No. 6,148,228.

(51) Int. Cl.$^7$ .............................................. A61B 5/0402
(52) U.S. Cl. ....................................................... 600/508
(58) Field of Search ................................ 607/508, 509, 607/515–517, 519

(56) References Cited

U.S. PATENT DOCUMENTS 5,649,544 A * 7/1997 Feng ........................... 600/509
6,148,228 A * 11/2000 Fang et al. .................. 600/509

* cited by examiner

*Primary Examiner*—George R. Evanisko
(74) *Attorney, Agent, or Firm*—Trojan Law Offices

(57) ABSTRACT

A method is delineated for detecting and locating coronary artery and heart disease comprising the steps of obtaining electrocardiograph (EKG) signals from a patient, modifying the EKG signals, and establishing a base value for use in evaluating modified EKG signals. The step of modifying includes the steps of amplifying the EKG signals, digitizing amplified EKG signals, mathematically modifying the amplified and digitized EKG signals to obtain 12 lead signals in the time domain, and converting the 12 lead signals into power spectrum signals in the frequency domain. The base value is obtained by taking a patient's resting heart rate in beats per minute, converting it to beats per second, and multiplying by a scaling quantity between approximately 3 and 7, inclusively. Then, a first area is calculated by integrating a selected one of the power spectrum signals from zero Hertz to the base value. Similarly, a second area results from integrating the selected power spectrum signal from the base value to infinity. Then, one takes the ratio of the first to second areas to obtain an evaluation standard indicative of the patient's coronary health. Peak analysis of the power spectrum signals is also available, and a scheme for locating detected heart disease is also provided. Lastly, a system corresponding to the aforementioned methodology is shown.

7 Claims, 8 Drawing Sheets

SYSTEM AND METHOD FOR DETECTING AND LOCATING HEART DISEASE

This application is a continuing application of U.S. patent application Ser. No. 09/035,476, which was filed on Mar. 5, 1998 and issues into U.S. Pat. No. 6,148,228 on Nov. 14, 2000.

BACKGROUND OF THE INVENTION

1. Field of the Invention

This invention is in the field of cardiology and methods therefor and, more particularly, is a system and method for detecting and locating heart disease, and especially coronary artery disease including myocardial ischaemia and infarction; however, the act of locating is with reference to myocardial ischemia and infarction.

2. Description of the Related Art

Coronary artery disease is the leading cause of death in the United States, yet the disease remains "silent" or dormant in the majority of patients until the fourth or fifth decade of life. At that point, coronary artery disease typically moves from the "silent" phase to a symptomatic phase, at which time the patient may experience as the first symptoms, angina pectoris, myocardial infarction, and/or sudden death.

The prevalence of coronary artery disease in the United States has been estimated as affecting over 4 million persons. Over 1 million are expected to suffer myocardial infarctions or sudden death before attaining the age of 60. Furthermore, once coronary artery disease is symptomatic— regardless of whether the symptoms comprise angina or myocardial infarction—the mortality rate is increased to 4% per year overall and 8% per year in those patients with an abnormal electrocardiogram or hypertension. This increased mortality rate is largely due to increases in the occurrence of sudden death, or the complications of repeated myocardial infarction.

Prior approaches to diagnose coronary artery disease fall into four general categories, which will be briefly discussed below. The first category falls under noninvasive, conventional EKG type tests, like the standard 12 lead EKG. Also, in this first category, some have practiced 24 hour ambulatory monitoring of the conventional EKG and stress test (see U.S. Pat. No. 3,267,934 to Thornton). This category of tests give ST segment depression and elevation readings as an indicator of myocardial ischaemia. However, ST segment changes are only sensitive to some portion of coronary artery diseases. Accordingly, tests such as these have limited value for the diagnosis of coronary artery disease, as they are relatively insensitive in detection of certain potential events. A second group of approaches to detect coronary artery disease involves more expensive noninvasive tests, such as nuclear imaging. Also, this cluster in of approaches may involve an invasive assessment of cardiac catheterization and coronary angiography. This second group of tests has the disadvantage of being expensive and/or invasive.

A third approach to the detection of coronary artery disease involves the use of software programs to analyze conventional EKGs. One such approach is the cardiointegram (CIG) which applies a process of integration over various sections of the QRST signal. The High Frequency Electrocardiogram (HFECG) is another software-based method which derives high frequency components of the EKG following a fast-Fourier transformation. The methods of this third group of approaches are either performed on every single heart beat or on the averaged QRS complex. When analyzing single heart beats, much potentially meaningful information is simply not evaluated. On the other hand, techniques based on analyzing a single averaged QRS complex seem to be able to distinguish minor signal changes from noise, but there are significant limitations to these types of methods as well. For example, the averaged EKG is based on the QRS superimposition, and the precision of superimposition is limited by sample rate, QRS identification software, analytical experience of the user, and heart rate variability. Accordingly, use of this third group of analysis techniques is also limited in terms of effectiveness at fully and accurately detecting coronary artery disease.

A fourth technique is exemplified by an article entitled "The Theoretical Basis and Clinical Study of EKG Multiphase Information (EMP1) System" (for The American Society of Hypertension, Sixth Scientific Meeting by Dan Qun Fang et al.), and by U.S. Pat. No. 5,509,425, entitled "Arrangement for and Method of Diagnosing and Warning of a Heart Attack." In this a approach, power spectrum and other frequency domain analyses are used to extract additional information from a conventional EKG; however, this technique also has its shortcomings. Specifically, Fourier transformation of the time domain signals into the frequency domain is conducted on only two EKG leads, namely lead V5 and lead II, thereby unnecessarily forfeiting the very potentially beneficial analyses of the remaining EKG leads. Additionally, this approach failed to establish use of a base value (as set forth in the current invention) in its analysis of power spectrum signals.

Therefore, there existed a need to provide a system and method for improved detection of coronary artery and heart disease. Moreover, the instant invention provides a system and method for not only detecting coronary artery and heart disease, but also locating such ailments, when detected.

SUMMARY OF THE INVENTION

An object of the present invention is to provide an improved system for detecting coronary artery and heart disease and a method therefor.

Another object of the present invention is to provide a system for locating the source or sources of detected coronary artery and heart disease and a method therefor.

Yet another object of the present invention is to provide a system for detecting and locating the source or sources of coronary artery and heart disease by analyzing at least one, and preferably all, of 12 lead signals transformed into power spectrum signals in the frequency domain.

Still another object of the present invention is to provide a system for detecting and locating the source or sources of coronary artery and heart disease by using a base value, derived from a patient's heart rate, in analyzing at least one, and preferably all, of 12 lead signals transformed into power spectrum signals in the frequency domain.

BRIEF DESCRIPTION OF THE PREFERRED EMBODIMENTS

According to one embodiment of the present invention, a method for detecting and locating heart disease is disclosed comprising the steps of obtaining electrocardiograph (EKG) signals from a patient, modifying the EKG signals, and establishing a base value for use in evaluating modified EKG signals. The step of obtaining includes the steps of providing an electrocardiograph, providing a plurality of connectors between a plurality of locations on the patient and the electrocardiograph, and operating the electrocardiograph to take readings from the plurality of locations and to output the EKG signals. Note that the plurality of locations include positions proximate the patient's Right Arm (RA), Left Arm (LA), Right Foot (RF), Left Foot (LF), and six separate areas on the patient's Chest (C1–C6).

The step of modifying includes the steps of mathematically modifying the EKG signals to obtain altered signals in the time domain, and converting the altered signals in the time domain into power spectrum signals in the frequency domain. Additionally, note that the step of modifying further includes the steps of amplifying the EKG signals, and digitizing amplified EKG signals. The altered signals in the time domain comprise at least one of 12 lead signals, namely, lead I, lead II, lead III, lead aVR, lead aVL, lead aVF, lead V1, lead V2, lead V3, lead V4, lead V5, and lead V6.

The step of establishing the base value comprises the steps of obtaining the patient's heart rate, and applying a conversion factor to the heart rate to obtain the base value. The step of obtaining the patient's heart rate comprises at least one of measuring the patient's heart rate, and acquiring the patient's heart rate from data relating to physical and medical characteristics of the patient. Preferably, one's heart rate comprises the patient's resting heart rate. The step of applying the conversion factor comprises the steps of converting the heart rate defined in beats per minute to beats per second, and multiplying the heart rate defined in beats per second by a scaling quantity. The scaling quantity comprises any number between approximately three and seven, inclusively, however, note that the scaling quantity preferably comprises the number five.

The present method further comprises the steps of calculating a first area by integrating a selected one of the power spectrum signals from zero Hertz to the base value, calculating a second area by integrating the selected one of the power spectrum signals from the base value to infinity, and dividing a first calculated value corresponding to the first area by a second calculated value corresponding to the second area to obtain al evaluation standard corresponding to the selected one of the power spectrum signals. A first state of the evaluation standard comprises a value of approximately$\geq$one to indicate a healthy state for the patient, and a second state of the evaluation standard comprises a value of approximately<one to indicate an unhealthy state for the patient. The present method further includes the step of obtaining a separate evaluation standard for each of the power spectrum signals in the frequency domain.

Additionally, the present method comprises the step of analyzing peaks for each of the power spectrum signals in the frequency domain against a plurality of evaluative standards for the peaks. The evaluative standards for the peaks include at least one, and preferably all, of determining if a second peak is greater in magnitude than a first peak for any of the power spectrum signals as indicative of an unhealthy state for the patient, determining if a fifth peak is greater in magnitude than the first peak for any of the power spectrum signals as indicative of an unhealthy state for the patient, determining if the fifth peak is greater in magnitude than a third peak for any of the power spectrum signals as indicative of an unhealthy state for the patient, determining if a fourth peak is greater in magnitude than the third peak for any of the power spectrum signals as indicative of an unhealthy state for the patient, determining if the first peak is relatively low in magnitude for any of the power spectrum signals as indicative of an unhealthy state for the patient, determining if the third peak is relatively low in magnitude for any of the power spectrum signals as indicative of an unhealthy state for the patient, determining if the first, second, third, and fourth peaks are relatively low in magnitude for any of the power in spectrum signals as indicative of an unhealthy state for the patient, and determining if the first, second, third, and fourth peaks are relatively high in magnitude for any of the power spectrum signals as indicative of an unhealthy state for the patient. Note that the aforementioned first, second, third, fourth, and fifth peaks correspond to the first five consecutive peaks in any of the power spectrum signals as viewed moving up in frequency from zero Hertz in the frequency domain.

The methodology for locating the heart disease comprises the steps of providing a plurality of locating standards wherein each locating standard corresponds to a distinct location of potential heart disease, and evaluating each locating standard of the plurality of locating standards to determine whether any distinct locations have heart disease. The step of providing a plurality of locating standards comprises the step of establishing a sum of different evaluation standards for each locating standard of the plurality of locating standards. Moreover, the step of evaluating each locating standard comprises the steps, repeated for each locating standard, of adding the sum of different evaluation standards for the selected locating standard, comparing the sum to the number of evaluation standards comprising the sum for the selected locating standard to determine whether the sum is$\geq$the number of evaluation standards, and to determine whether the sum is<the number of evaluation standards, assigning the distinct location of the potential heart disease corresponding to the selected locating standard with a determination of an unhealthy state for the patient when the sum is<the number of evaluation standards, and assigning the distinct location of the potential heart disease corresponding to the selected locating standard with a determination of a healthy state for the patient when the sum is$\geq$the number of evaluation standards. The plurality of locating standards and their corresponding distinct locations of potential heart disease define an analysis table comprising: (1) V1+V2+V3+V4$\leq$Anteroseptal, (2) V2+V3+V4+V5$\leq$Anterior, (3) II aVF+V1+V2$\leq$Inferior Posterior, (4) I+aVL+V3+V4+V5+V6$\leq$Anterolateral, (5) I+aVL+V5+V6$\leq$Lateral, (6) I+aVR+aVL+V6$\vert$Lead I Area, (7) II+aVR+aVF$\leq$Lead II Area, (8) III+aVL+aVF$\leq$Lead III Area, (9) I+II+aVR+V5$\leq$Lead aVR Area, (10) I+III+aVL$\leq$Lead aVL Area, (11) II+III+aVR$\leq$Lead aVF Area, (12) V1+V2+V6$\leq$Lead V1 Area, (13) V1+V2+V3$\leq$Lead V2 Area, (14) V2+V3+V4$\leq$Lead V3 Area, (15) V3+V4+V5$\leq$Lead V4 Area, (16) V4+V5+V6$\leq$Lead V5 Area, (17) V1+V5+V6$\leq$Lead V6 Area, 9

18) V1+V2$\leq$Septal, and (19) II+aVF$\leq$Inferior. Note that the corresponding distinct locations of potential heart disease identified above are well known to those skilled in the art.

Note that when the sum is$\geq$its corresponding number of evaluation standards for each locating standard of the plurality of locating standards, no distinct location of potential heart disease is detected. When the sum is<its corresponding number of evaluation standards for only one locating standard of the plurality of locating standards, the distinct location corresponding to that one locating standard has detected heart disease. When the sum is<its corresponding number of evaluation standards for more than one locating standard of the plurality of locating standards, each distinct location corresponding to those "more than one locating standard" of the plurality of locating standards has detected heart disease. When a plurality of locating standards have their sums<their corresponding number of evaluation standards, the most accurate prediction of the distinct location for the detected heart disease corresponds to the locating standard of the plurality of locating standards with their sums<their corresponding number of evaluation standards that is located highest on the analysis table. Then, the remaining locating standards of the plurality of locating standards having their sums<their corresponding number of evaluation standards are of lesser accuracy in completely locating the area of detected heart disease as their corresponding distinct locations move down the analysis table. In other words, a for the plurality of locating standards with their sums<their corresponding number of evaluation standards, the corresponding distinct locations of detected heart disease are listed from most to least accurate in fully and completely locating the heart disease, from the top to the bottom of the analysis table.

Note that in the present invention, at least one but less than all of the plurality of locating standards may be evaluated to determine whether any of the distinct locations have heart disease. Alternatively, all of the plurality of locating standards may be evaluated to determine whether any of the distinct locations have heart disease. In the preferred embodiment of the present invention, all of the 12 lead signals are simultaneously and continuously obtained over a period of time for the step of converting the altered signals in the time domain into the power spectrum signals in the frequency domain; however, less than all of the 12 lead signals may be procured as noted. Generally, the period of time comprises a duration in excess of one second; however, the period of time preferably comprises a duration of approximately 88 seconds.

According to another embodiment of the present invention, a system for detecting and locating heart disease is disclosed comprising, in combination, means for obtaining electrocardiograph (EKG) signals from a patient, means for modifying the EKG signals coupled to the means for obtaining, and means for establishing a base value for use in evaluating modified EKG signals. The means for modifying further includes means for amplifying the EKG signals, means for digitizing amplified EKG signals, and a processor coupled to the means for digitizing. The processor includes means for mathematically modifying the EKG signals to obtain altered As signals in the time domain, and means for converting the altered signals in the time domain into power spectrum signals in the frequency domain. Note that the altered signals in the time domain comprise at least one of 12 lead signals, namely, lead I, lead II, lead III, lead aVR, lead aVL, lead aVF, lead V1, lead V2, lead V3, lead V4, lead V5, and lead V6.

The means for establishing a base value comprises means for obtaining the patient's heart rate, and means for applying a conversion factor to the heart rate to obtain the base value. The means for applying the conversion factor comprises means for converting the heart rate defined in beats per minute to beats per second, and means for multiplying the heart rate defined in beats per second by a scaling quantity. The scaling quantity comprises any number between approximately three and seven, inclusively, however, the scaling quantity preferably comprises the number five.

The processor further includes means for calculating a first area by integrating a selected one of the power spectrum signals from zero Hertz to the base value, means for calculating a second area by integrating the selected one of the power spectrum signals from the base value to infinity, and means for dividing a first calculated value corresponding to the first area by a second calculated value corresponding to the second area to obtain an evaluation standard corresponding to the selected one of the power spectrum signals. A first state of the evaluation standard comprises a value of approximately $\geq$ one to indicate a healthy state for the patient, and a second state of the evaluation standard comprises a value of approximately<one to indicate an unhealthy state for the patient.

The foregoing and other objects, features, and advantages of the invention will be apparent from the following, more particular, description of the preferred embodiments of the invention, as illustrated in the accompanying drawings.

DESCRIPTION OF THE PREFERRED EMBODIMENTS

Figure 1A:
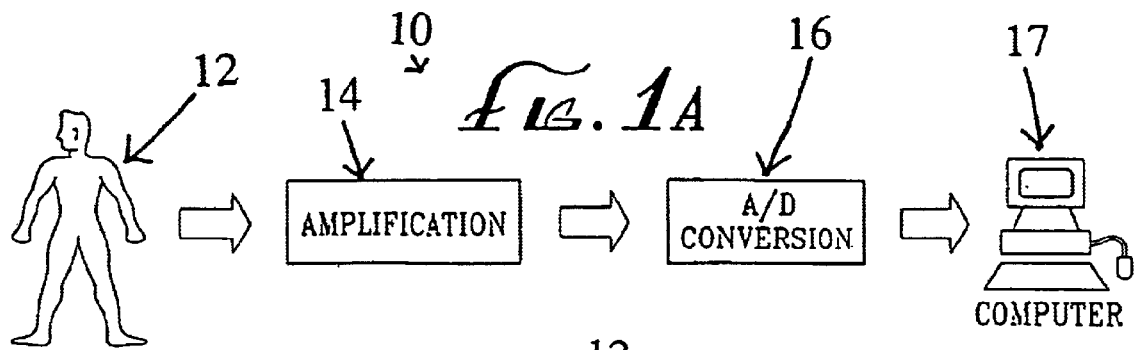
FIG. 1A is a simplified conceptual view demonstrating a portion of the system and method of the present invention.

Referring to FIG. 1A, a simplified conceptual view is shown illustrating a portion of the system and methodology, as generally designated by reference number 10, of the present invention. A conventional electrocardiograph (not shown) is connected to a plurality of locations (see FIG. 1B) on the patient 12. EKG signals are generated by the electrocardiograph in a manner well known to those skilled in the art. Those EKG signals are then provided to logical block 14 for amplification. The details of the amplification block 14 are delineated in FIGS. 6A–6B; however, note that any one of a plurality of different amplification schemes well known to those skilled in the art could be implemented in system or method 10, if desired. The amplified EKG signals are then provided to an Analog to Digital (A/D) converter 16, which is shown in greater detail in FIG. 7. Here again, the details (as shown in FIG. 7) of the A/D converter 16 are shown only by way of example, as any one of a plurality of different AID it t converters well known to those skilled in the relevant art could be included in system or method 10, if so desired. The digitized EKG signals are then provided to a computer 17, which in the preferred embodiment includes a processor and other typical computer processing components, a monitor, a keyboard, a mouse, and potentially any other typical input/output component or device associated with a computer.

Figure 1B:
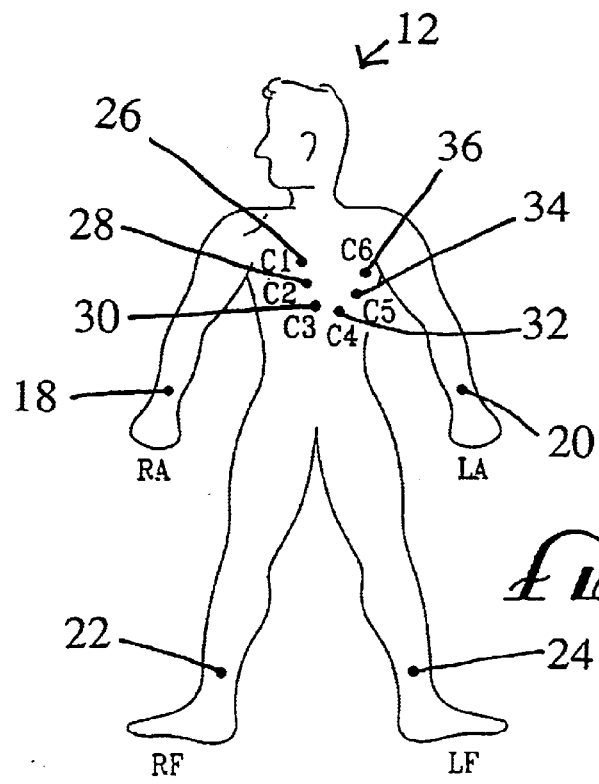
FIG. 1B is a simplified view representing 10 separate approximate locations for affixing the ends of standard EKG connectors to a patient.

Referring to FIG. 1B, a simplified view is shown representing 10 separate approximate locations for affixing the ends of standard EKG connectors to the patient 12. These locations are well known to those skilled in the art. They include a Right Arm (RA) location 18, a Left Arm (LA) location 20, a Right Foot (RF) location 22, a Left Foot (LF) location 24, and six Chest locations (C1–C6) corresponding to reference numbers 26–36.

Figure 2:
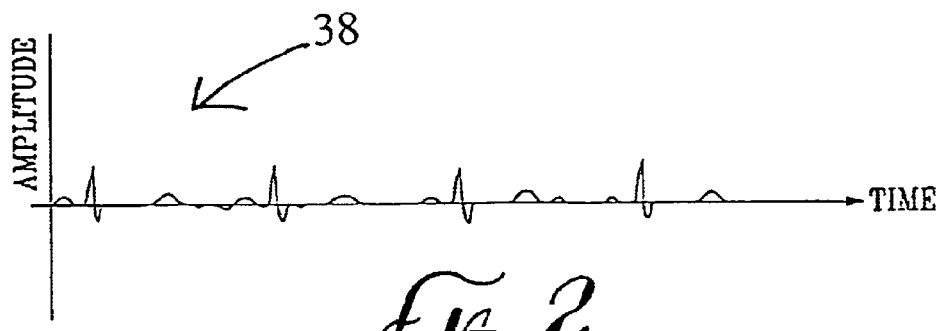
FIG. 2 is a simplified graphical depiction of one lead of a conventional (standard) EKG shown versus time.

Referring to FIG. 2, a simplified graphical depiction of one lead of a conventional (standard) EKG is shown versus time. The repetitive, individual peaks are representative of a patient's heart beat, as those skilled in the art realize. Additional information can be gleaned from such a plot; however, that exercise is well known to those skilled in the art, and is not tile focus of the present invention, so it will not be discussed in further detail herein.

Figure 3:
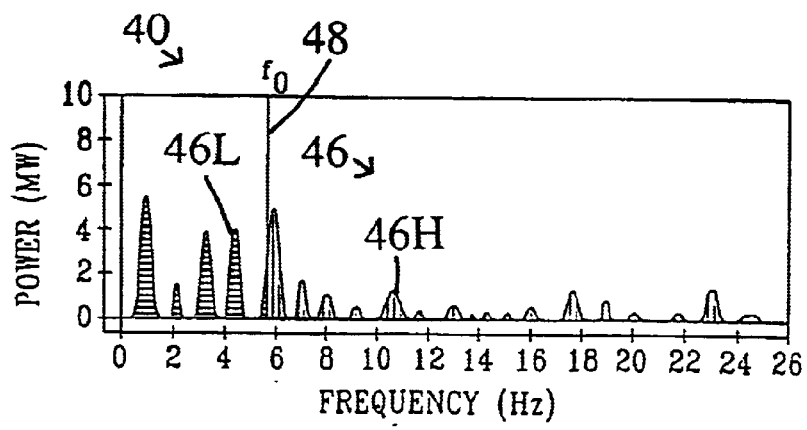
FIG. 3 is a simplified graphical depiction of one lead of a power spectrum signal in the frequency domain. Note that in this example, the base value ($f_o$) is shown as approximately six Hertz.

Referring to FIG. 3, a simplified graphical depiction of one lead of a power spectrum signal in the frequency domain is shown. The plot itself is designated by reference number 40, while the power spectrum signal is referenced by number 46. Note that, at present, there are 12 standard leads produced pursuant to standard EKG analysis, and plot 40 represents one of those 12 lead signals having been converted to the power spectrum signal 46 in the frequency domain. The frequency domain is indicated by the horizontal axis of plot 40 shown in frequency units of Hertz, while the vertical axis is demarcated in power units of milliwatts. The base value of $f_0$ is referenced by number 48, and it delineates a separation between two separate areas under power spectrum signal 46. The first area 46L (where "L" indicates lower frequencies) comprises the area under power spectrum signal 46 from zero Hertz to $f_0$ 48, while the second area 46H (where "H" indicates higher frequencies) comprises the area under power spectrum signal 46 from $f_0$ 48 to infinity. Area one is indicated by the horizontal shading lines located to the left of $f_0$ 48 under power spectrum signal 46, and area two is indicated by the solid shading located to the right of $f_0$ 48 under power spectrum signal 46. The particular manner of establishing and using base value $f_0$ 48, as well as areas one 46L and two 46H, will be described in greater detail in the operational discussion of the present invention 10.

Figure 4:
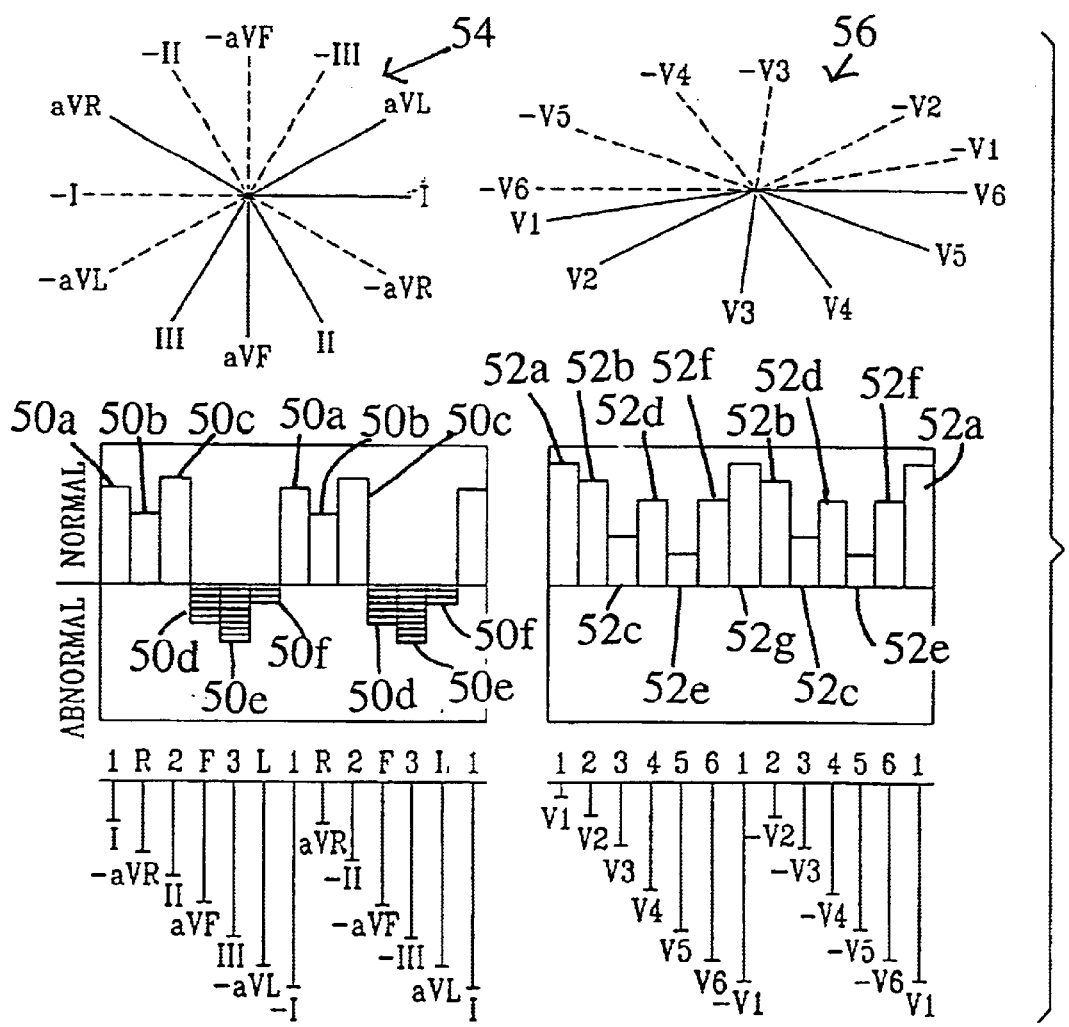
FIG. 4 is a simplified graphical depiction of the 12 evaluation standards. Note that a first group of 6 of the 12 evaluation standards is shown (in repetitive form) in one of the two tables shown, while a second group of 6 of the 12 evaluation standards is shown (also in repetitive form) in the other table. Located above the pair of tables are two representations of a patient's heart, as illustrated by two sets of intersecting lines.

Referring to FIG. 4, a simplified graphical depiction of the 12 evaluation standards is shown. As mentioned with respect to FIG. 3, there are 12 lead signals associated with standard EKG analysis. At least one, but preferably all, of the 12 lead signals are converted to their corresponding power spectrum signals in the frequency domain as shown by way of example in FIG. 3. For each of the 12 power spectrum signals, a ratio is taken of their corresponding lower and higher frequency areas (i.e., 46L/46H from FIG. 3) to arrive at their corresponding evaluation standards. In other words, one divides the lower frequency area 46L by the higher frequency area 46H to attain the evaluation standard for a given power spectrum signal, such as 46 in FIG. 3. This is preferably done for all 12 power spectrum signals, each somewhat like 46, corresponding to the 12 lead signals in standard EKG analysis to obtain the 12 evaluation standards.

Now focusing on the bottom left quadrant of FIG. 4, a simplified table or plot 50 is shown. A horizontal line 50g divides an upper portion of the display corresponding to normal or healthy conditions for a patient's heart from a lower portion of the display corresponding to abnormal or unhealthy conditions for the patient's heart. Moving from left to right across table 50 are a plurality of bars (i.e., evaluation standards) labelled 50a, 50b, 50c, 50d, 50e, 50f, 50a, 50b, 50c, 50d, 50e, 50f, and 50a. Note that 6 of the 12 evaluation standards, namely 50a–50f are repeatedly displayed on table 50 to ease understanding, and possibly detection and/or location, of heart abnormalities. Each of the 6 evaluation standards are computed as generally discussed above, and as will be covered in greater detail under the operational discussion of the present invention 10. The 6 evaluation standards shown in table 50 correspond to 6 power spectrum signals for 6 EKG lead signals, namely lead I, lead aVR, lead II, lead aVF, lead, III, and lead aVL. As indicated by the labels at the bottom of table 50 , lead I corresponds to bar 50a, lead aVR corresponds to bar 50b, lead II corresponds to bar 50c, lead aVF corresponds to bar 50d, lead III corresponds to bar 50e, and lead aVL corresponds to bar 50f. Thereafter, bars 50a–50f are repeated, as shown, to ease analysis of table 50.

For each evaluation standard, when the corresponding ratio is approximately greater than or equal to one, a healthy or normal state for the patient's heart is detected, and the ratio value thus obtained is plotted for the corresponding bar on table 50. If however, the computed aid evaluation standard ratio is approximately less than one, then the patient's heart has a detected abnormality or unhealthy state. In table 50, by way of example, the test patient has heart abnormalities corresponding to the evaluation standards for the power spectrum signals of lead aVF corresponding to bar 50d, lead III corresponding to bar 50e, and lead aVL corresponding to bar 50f. Bars 50d–50f are shown below line 50g in the abnormal range. Note that there are no markings shown along the vertical axis of table 50; however, appropriate markings could be shown, if desired. Nonetheless, note that the lengths of the abnormal bars 50d–50f are short, as compared to those for the normal bars 50a–50c. This is indicative of the fact that the evaluation standard ratios for the abnormal bars 50d–50f are less than one, while the evaluation standard ratios for the normal bars 50a–50c are approximately greater than or equal one. Lastly, note that while bars 50a–50f are shown in a particular order, and in repetitive form, it is considered within the scope of the present invention 10 to have evaluation standard ratios shown in different combinations, with or without repetition.

Now focusing on the upper left quadrant of FIG. 4, a simplified representation of a patient's heart is shown by the pairs of intersecting lines 54. Those skilled in the art understand such a depiction, so detailed discussion of this portrayal is omitted other than to note the correspondence between the heart representation 54 and table 50. In particular, the 6 evaluation standards show in table 50 correspond to the same 6 leads in representation 54, namely lead I, lead aVR, lead II, lead aVF, lead, III, and lead aVL. Also, note that the 6 leads shown in representation 54 are shown in bipolar form (i.e., positive and negative).

Turning now to the right half of FIG. 4, a new and simplified table 52 is shown with its corresponding simplified heart representation 56. A discussion of table 52 and heart aid, representation 56 would be completely analogous to that already provided with respect to table 50 and heart representation 54. Accordingly, an abbreviated discussion of table 52 and heart representation 56 follows. A horizontal line 52g divides an upper portion of the display corresponding to normal or healthy conditions for a patient's heart from a lower portion of the display corresponding to abnormal or unhealthy conditions for the patient's heart. Moving from left to right across table 52 are a plurality of evaluation standard bars labelled 52a, 52b, 52c, 52d, 52e, 52f, 52a, 52b, 52c, 52d, 52e, 52f, and 52a. Note that 6 of the 12 evaluation standards, namely 52a–52f, are repeatedly displayed on table 52 to ease understanding, and possibly detection and/or location, of heart abnormalities. Each of the 6 evaluation standards are computed as generally discussed above, and as will be covered in greater detail under the operational discussion of the present invention 10. The 6 evaluation standards shown in table 52 correspond to 6 power spectrum signals for 6 EKG lead signals, namely lead V1, lead V2, lead V3, lead V4, lead, V5, and lead V6. As indicated by the labels at the bottom of table 52, lead V1 corresponds to bar 52a, lead V2 corresponds to bar 52b, lead V3 corresponds to bar 52c, lead V4 corresponds to bar 52d, lead V5 corresponds to bar 52e, and lead V6 corresponds to bar 52f. Thereafter, bars 52a–52f are repeated, as shown, to ease analysis of table 52.

For each evaluation standard, when the corresponding ratio is approximately greater than or equal to one, a healthy or normal state for the patient's heart is detected, and the ratio value thus obtained is plotted for the corresponding bar on table 52. If however, the computed evaluation standard ratio is approximately less than one, then the patient's heart has a detected abnormality or unhealthy state. In table 52, by way of example, tile test patient has no heart abnormalities, so none of the evaluation standard bars 52a–52f are shown in the abnormal range. Lastly, note that while bars 52a–52f are shown in a particular order, and in repetitive form, it is considered within the scope of the present invention 10 to have evaluation standard ratios shown in different combinations, with or without repetition.

Now focusing on the upper right quadrant of FIG. 4, another simplified representation of a patient's heart is shown by the pairs of intersecting lines 56. Those skilled in the art understand such a depiction, so detailed discussion of this portrayal is omitted other than to note the correspondence between the heart representation 56 and table 52. In particular, the 6 evaluation standards shown in table 52 correspond to the same 6 leads, in representation 56, namely lead V1, lead V2, lead V3, lead V4, lead, V5, and lead V6. Also, note that the 6 leads shown in representation 56 are shown in bipolar form (i.e., positive and negative).

Referring to FIGS. 5A–5H, each shows a simplified graphical depiction of a lead of a power spectrum signal in the frequency domain. Moreover, each demonstrates a different case representing at least a potential, if not an actual, heart disease problem. FIGS. 5A–5H represent eight different peak analysis techniques for detecting heart disease, and the specifics of these techniques will be discussed in greater detail under the operational discussion for the present invention 10.

Figure 6A:
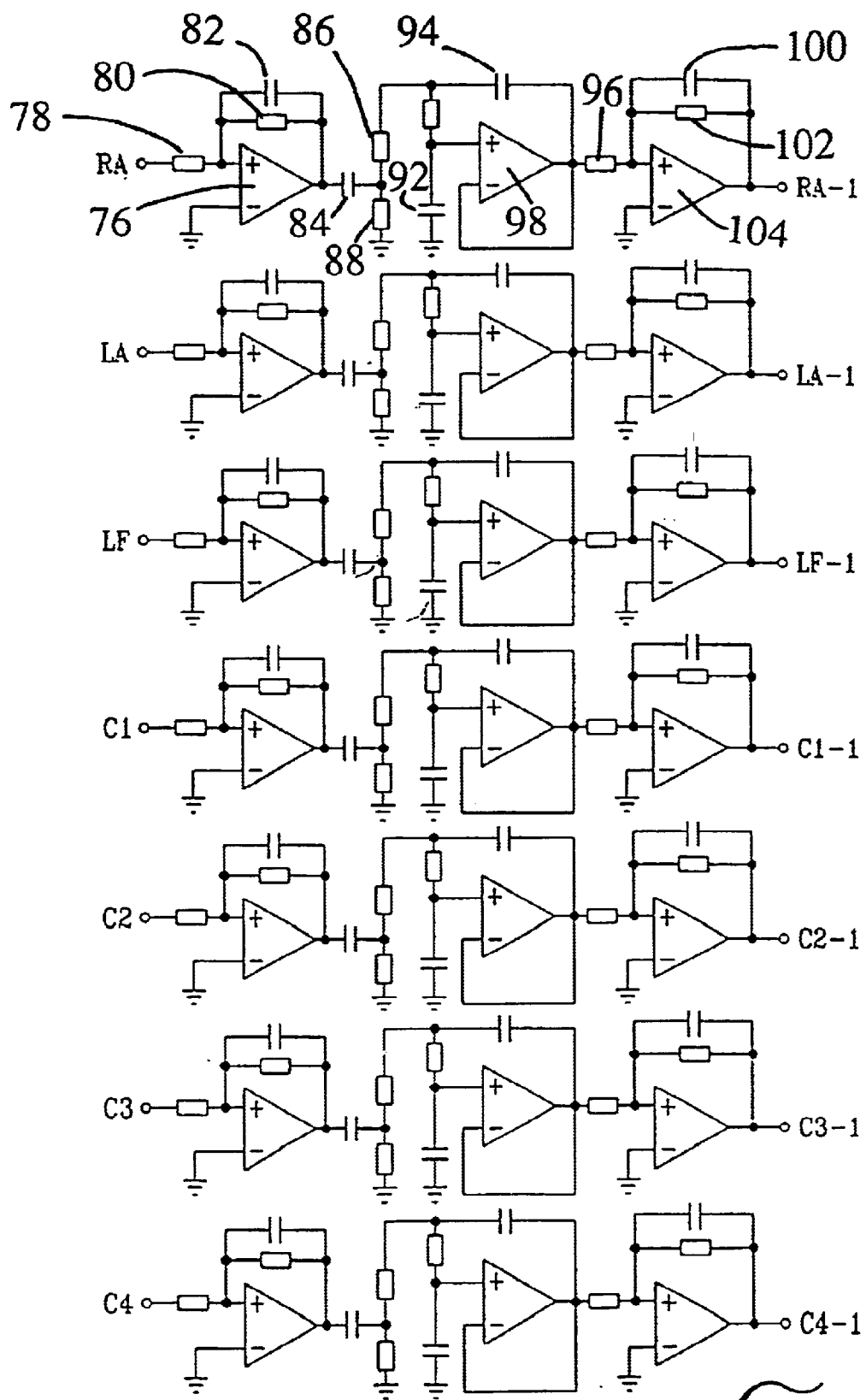
FIGS. 6A–6B together show, by way of example, amplification circuitry for the instant invention.
Figure 6B:
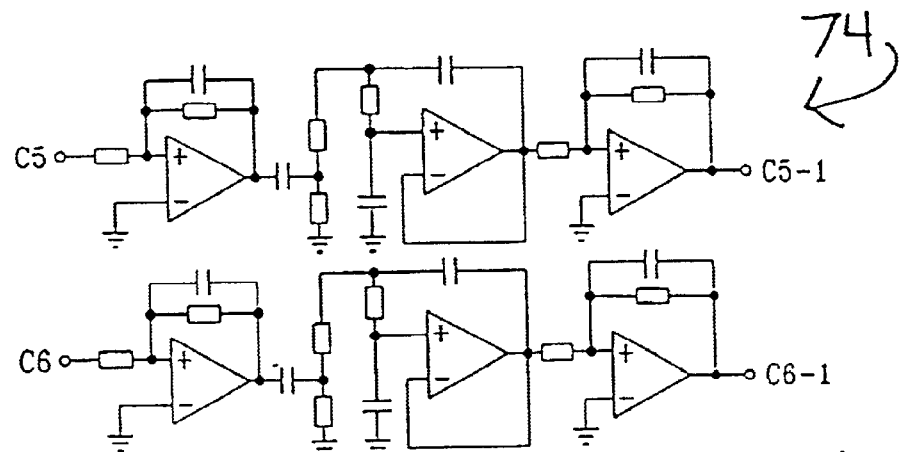
Figure 7:
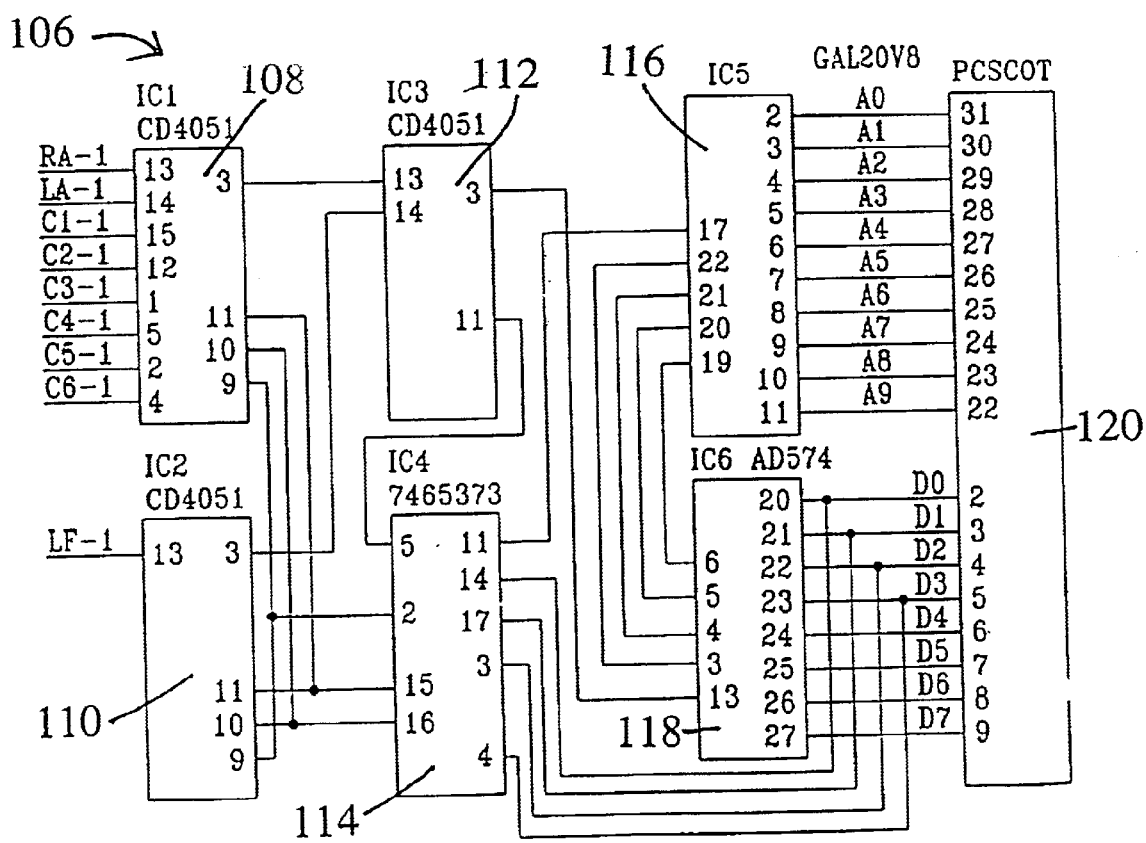
FIG. 7 shows, by way of example, analog to digital converter circuitry for the instant invention.

Referring to FIGS. 6A–6B, amplification circuitry 74 is shown, only by way of example, for use in the instant invention 10. Note that amplification circuitry 74 corresponds to the general amplification block 14 in FIG. 1A, but again, those skilled in the art will realize after understanding the purpose of amplification circuitry 74, that alternate amplification schemes could be implemented for block 14 in the present invention 10, if so desired. Upon review of FIGS. 6A–6B, one realizes that amplification circuitry 74 consists of 9 separate amplification chains wherein each is comprised of identical components. Thus, rather than repeating the discussion for each of the 9 separate amplification chains, one will be discussed, and the remaining 8 would be described in substantially the same manner.

By way of example then, looking at the first amplification chain in amplification circuitry 74, one sees three linked operational amplifiers (hereafter "op-amps") 76, 98, and 104. The EKG signal corresponding to the connection in proximity to a patient's right arm (see RA 18 in FIG. 1B) is coupled to a resistor 78. Preferably, resistor 78 has a value of approximately 430 KOhms. Resistor 78 is coupled at its other junction to the no inverting input of op-amp 76. The inverting input of op-amp 76 is tied to ground. The noninverting input of op-amp 76 is also coupled to first junctions of a capacitor 82 and resistor 80. In the preferred embodiment, resistor 82 has a value of approximately 20 KOhms, while capacitor S2 has a value of approximately 0.01 microfarads. The opposite junctions of capacitor 82 and resistor 80 are coupled to the output of op-amp 76. Also coupled to the output of op-amp 76 is capacitor 84 having an approximate value of 0.68 microfarads. The opposite junction of capacitor 84 is coupled between resistors 86 and 88 having approximate values of 33 KOhms and 2.2 MOhms, respectively. The other end of resistor 88 is tied to ground, while the opposite end of resistor 86 is tied to another resistor 90 and a capacitor 94. Resistor 90 has an approximate value of 20 KOhms, while capacitor 94 has an approximate value of 0.1 microfarads.

The opposite end of resistor 90 is coupled to both the noninverting input of op-amp 98 and to another capacitor 92 having an approximate value of 0.01 microfarads. The opposite junction of capacitor 92 is tied to ground. The inverting input of op-amp 98 is tied to its output and to an opposite junction of capacitor 94. The output of op-amp 98 is also coupled to a resistor 96 having an approximate value of 1 KOhms. The opposite end of resistor 96 is coupled to the noninverting input of op-amp 104, while the inverting input of op-amp 104 is tied to ground. The noninverting input of op-amp 104 is also coupled to a resistor 102 having an approximate value of 47 KOhms, and to a capacitor 100 having an approximate value of 0.01 microfarads. The opposite ends of capacitor 100 and resistor 102 are coupled to the output of op-amp 104, which provides the amplified and modified version (i.e., RA-1) of the chain's input RA. In a similar manner, eight other identical amplification chains take inputs LA, LF, C1, C2, C3, C4, C5, and C6 (from the patient 12 in FIG. 1B) and provide respective amplified and modified outputs LA-1, LF-1, C1-1, C2-1, C3-1, C4-1, C5-1, and C6-1.

Referring to FIG. 7, analog to digital converter circuitry 106 is shown for the instant invention 10. Note that the analog to digital circuitry 106 (hereafter "A/D circuitry") corresponds to the A/D conversion block 16 shown in FIG. 1A. Also note that A/D circuitry 106 is shown only by way of example, for those skilled in the art realize that there are many different types of A/D converters that could be implemented into the present invention 10, if so desired.

A/D circuitry 106 consists of 6 Integrated Circuit (IC) chips identified as IC1–IC6. Each IC chip is a product of Analog Devices, USA. Analog Device's part numbers for IC1–IC6 are as follows: 1) IC1-CD4051; 2) IC2-CD4051; 3) IC3-CD4051; 4) IC4-74LS373; 5) IC5-GAL20V8; and 6) IC6-AD574. Note that pertinent pin numbers for each of the IC chips are shown to define how they are interconnected. IC1 108 has inputs of RA-1, LA-1, C1-1, C2-1, C3-1, C4-1, C5-1, and C6-1 wherein these inputs are provided from the amplification circuitry 74 of FIGS. 6A–6B. Similarly, IC2 110 has as an input LF-1 also provided from the amplification circuitry 74. IC5 116 is coupled to a computer 17 (i.e., a PC slot 120) as previously shown in FIG. 1A. A plurality of connections are made between IC5 116 and the PC slot 120 of the computer 17 for addressing tasks over lines A0–A9. IC6 118 is also coupled to the PC slot 120 of the computer 17 via a plurality of lines D0–D7 for transferring data. Still with reference to FIG. 7, the 9 amplified and modified signals (i.e., RA-1, LA-1, LF-1, C1-1, C2-1, C3-1, C4-1, C5-1, and C6-1; hereafter the "nine signals") are input to IC1 108 and IC2 110, as indicated in the drawing, for selection. The appropriate computer address is translated over lines A0–A9 to IC5 116, and then assigned to IC6 118 at input pins 3–6. The nine signals are digitized in turn. The basic process involves communication over lines D0–D3 with IC4 114 to select the nine signals for digitization. The nine signals are switched to the input pin 13 of IC6 118 for digitization, whereby digital versions of the nine signals are then transferred to the computer 17 via computer slot 120 and data lines D0–D7. In the preferred embodiment the digitized data is transferred in 12 bit packets. Specifically, each 12 bit digitized data packet is sent to the computer 17 in two bursts, one of 8 bits and another of 4 bits. It is considered within the scope of the present invention 10 to either increase or decrease the digitized data packet size, as well as to alter the number of bits sent per burst.

IC1 108 and IC2 110 are controlled by signals emanating from pins 2, 15, and 16 of IC4 114. IC3 112 is controlled by signals emanating from pin 5 of IC4 114. Through this control, IC1 108 selects each of its 8 input signals, one at a time, and outputs them over output pin 3 to input pin 13 of IC3 112. As IC2 110 has only one input signal (i.e., LF-1), when selected, LF-1 is supplied over output pin 3 to input pin 14 of IC3 112. The nine signals provided between input pins 13 and 14 of IC3 112 will be selectively output, one at a time, over output pin 3 of IC3 112 to input pin 13 of IC6 118 for A/D conversion. Thus, the nine signals, after having been amplified and modified by the amplification circuitry 74 of FIGS. 6A–6B, are digitized and supplied to the computer (i.e., see 17 in FIG. 1A). Lastly, having identified each of the components and their interconnections for A/D circuitry 106, a more detailed discussion of the component internals is deemed unnecessary. Additionally, as the A/D circuitry 106 could be omitted in lieu of another A/D converter well known to those skilled in the art, a more detailed discussion of both the general operation of an A/D converter and the specific internals of IC1–IC6 is not required.

OPERATION

Figure 8:
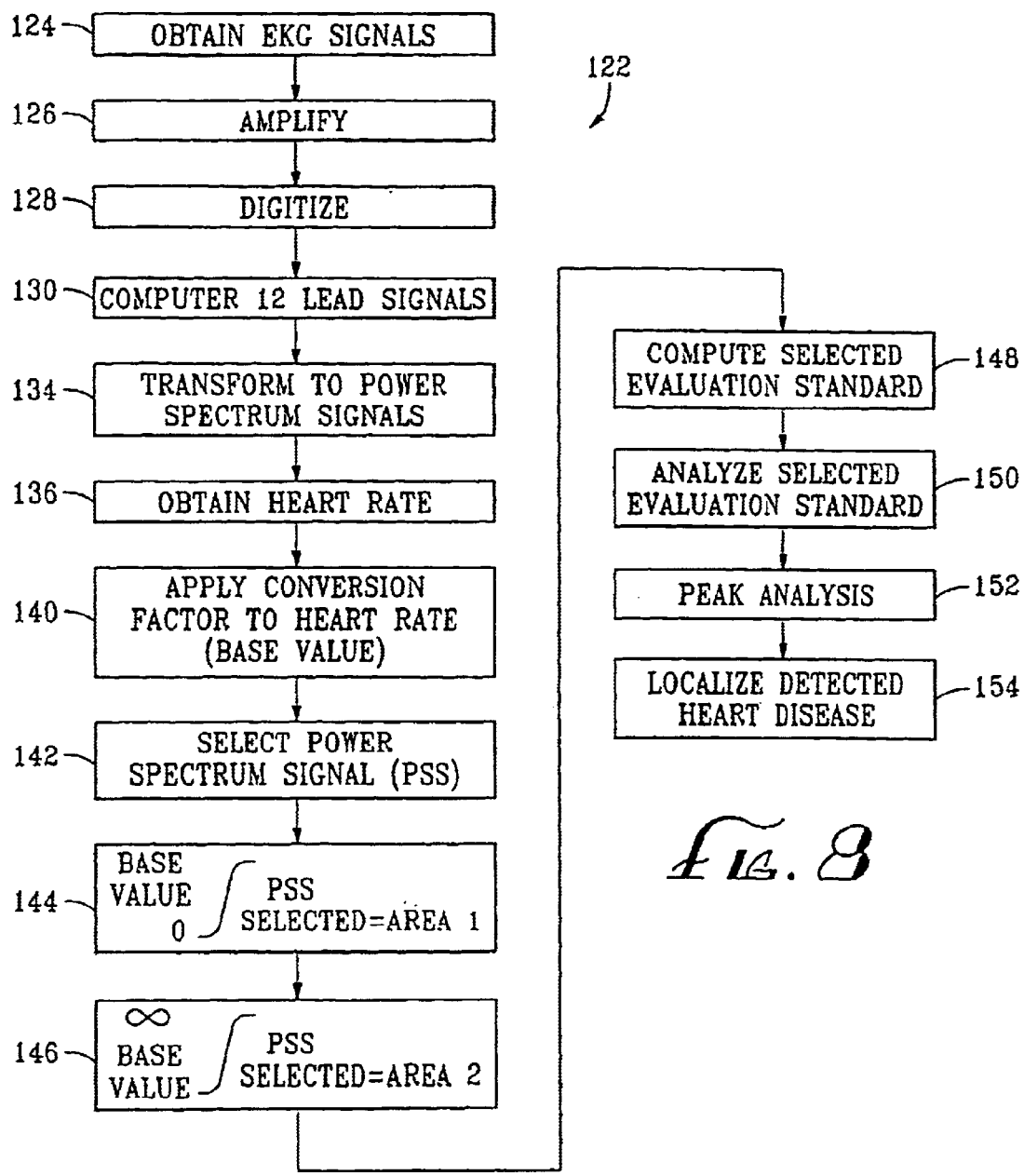
FIG. 8 depicts a simplified, block diagram view of the methodology and system organization for the present invention.

Before launching into a detailed operational discussion, consideration of FIG. 8 provides a helpful, broad understanding of the present invention 122 (or see 10 in FIG. 1A). Logical block 124 indicates that one must first obtain EKG signals, which are then amplified and digitized in respective logical blocks 126 and 128. Next, the digitized signals are used to compute the 12 lead signals in logical block 130. The 12 lead signals are then transformed into corresponding power spectrum signals in logical block 134. Logical block 136 represents is the requirement of obtaining the patient's heart rate. A conversion factor is applied to the patient's heart rate to obtain the base value, as represented by logical block 140. At this point, any one of the 12 power spectrum signals is selected pursuant to logical block 142. Logical blocks 144 and 146 represent the integration of the selected power spectrum signal to compute the first and second areas under the curve, respectively. Using the computed areas, logical block 148 calculates the evaluation standard for the selected power spectrum signal. Thereafter, analysis of the evaluation standard corresponding to the selected power spectrum signal occurs pursuant to logical block 150. Logical blocks 152 and 154 then provide the additional options of executing peak analysis of the selected power spectrum signal, and localizing detected heart disease, respectively. Note that in the preferred embodiment of the present invention 122, logical blocks 144–154 would be performed on all 12 power spectrum signals; however, if desired, less than 12 power spectrum signals may be evaluated.

Now beginning a more comprehensive discussion of the method embodiment for the present invention 122, an overview of the instant method for detecting and locating heart disease includes the steps of obtaining electrocardiograph (EKG) signals from a patient 12 (see FIG. 1A), modifying the EKG signals, and establishing a base value for use in evaluating modified EKG signals. The step of obtaining includes the steps of providing an electrocardiograph (not shown, but would be coupled to the patient 12 in FIG. 1A), providing a plurality of connectors (not shown) between a plurality of locations (see 18–36 in FIG. 1B) on the patient 12 and the electrocardiograph, and operating the electrocardiograph to take readings from the plurality of locations 18–36 and to output the EKG signals. As indicated, the electrocardiograph is not shown; this was for the sake of simplification of the drawings. Additionally, note that electrocardiographs and their manner of operation to obtain EKG signals are well known to those skilled in the art. Focusing on FIG. 1B, the noted plurality of locations, which are well known to those skilled in the art, include positions proximate the patient's Right Arm (RA) 18, Left Arm (LA) 20, Right Foot (RF) 22, Left Foot (LF) 24, and six separate areas on the patient's Chest (C1–C6) 26–36.

The step of modifying further includes the steps of amplifying the EKG signals, and digitizing amplified EKG signals, as represented by logical blocks 14 and 16 in FIG. 1A, or logical blocks 126 and 128 in FIG. 8, respectively. As previously indicated amplification may be provided by the amplification circuitry 74 shown in FIGS. 6A–6B; however, any one of a number of different amplification schemes well known to those skilled in the art could be substituted, if desired. Also, as previously indicated, each of the amplification chains in FIGS. 6A–6B takes its respective input, and provides an amplified, modified output. For example, the first amplification chain shown at the top of FIG. 6A takes the EKG signal RA (see 18 from FIG. 1B) and provides RA-1 as the chain's output. No further discussion of the operation of amplification circuitry 74 is provided, other than what has been previously provided, as operation of such circuitry is well known to those skilled in the art.

The amplified, modified EKG signals are then digitized, as represented by logical block 16 in FIG. 1A or logical block 128 in FIG. 8. As mentioned previously, the internals of these logical blocks 16 or 128 may be provided by the A/D circuitry 106, as shown in FIG. 7. Nonetheless, those skilled in the art realize that any one of a plurality of A/D converters well known to those skilled in the art may be substituted, if so desired. Additional discussion of the operation of A/D circuitry 106, other than what has been previously provided, is deemed unnecessary as operation of such circuitry is well known to those skilled in the art.

The step of modifying further includes the steps of mathematically modifying the EKG signals to obtain altered signals in the time domain, and converting the altered signals in the time domain into power spectrum signals in the frequency domain. Initially, the electrocardiograph provides conventional, unaltered EKG signals. Then, these signals are modified to obtain the "altered" signals in the time domain. The modification may include the amplification and digitization of the EKG signals mentioned above. Additionally, this modification of the conventional EKG signals includes mathematical modification to obtain 12 lead signals in the time domain. Note that these 12 lead signals are well known to those skilled in the art; however, for the sake of absolute clarity, the following table is provided in which 12 separate equations establish the mathematical relationship between the 12 lead signals and the standard EKG signals (taken from the points indicated on patient 12 in FIG. 1B):

| LEAD | | EKG SIGNALS: |
|---|---|---|
| I | = | LA-RA |
| II | = | LF-RA |
| III | = | LF-LA |
| aVR | = | RA-(RA + LA + LF)/3 |
| aVL | = | LA-(RA + LA + LF)/3 |
| aVF | = | LF-(RA + LA + LF)/3 |
| V1 | = | C1-(RA + LA + LF)/3 |
| V2 | = | C2-(RA + LA + LF)/3 |
| V3 | = | C3-(RA + LA + LF)/3 |
| V4 | = | C4-(RA + LA + LF)/3 |
| V5 | = | C5-(RA + LA + LF)/3 |
| V6 | = | C6-(RA + LA + LF)/3 |

Simply put then, the conventional, unmodified (i.e., other than possibly amplified and digitized) EKG signals are combined in accordance with the equations above to arrive at the 12 lead signals in the time domain. Thus, the "altered" signals in the time domain comprise the 12 lead signals (although, if desired, less than all 12 may be computed), and note that the conventional, unmodified EKG signals are typically altered by amplification and digitization prior to being altered into the 12 lead signals in the time domain. Next, the 12 lead signals in the time domain (if, as assumed hereafter, that all 12 are used) are converted into power spectrum signals in the frequency domain in accordance with the following equation:

$$P[i]=S[i](f)\cdot S[i](f)^*$$

Here, P[i] represents the "ith" calculated power spectrum signal where "i" corresponds to the selected power spectrum signal (i.e., there are 12 power spectrum signals corresponding to the 12 lead signals). Each power spectrum signal is in the frequency domain. S[i](f) represents the Fourier transform, in the frequency domain, taken on the "ith" one of the 12 time domain lead signals, and S[i](f)* is the complex conjugate of S[i](f). In summary, one takes the 12 lead signals in the time domain, and then using the formula above for P[i], arrives at 12 power spectrum signals in the frequency domain corresponding to the 12 time domain lead signals.

The aforementioned method step of establishing the base value comprises the steps of obtaining the patient's heart rate, and applying a conversion factor to the heart rate to obtain the base value. Obtaining the patient's heart rate is preferably accomplished by measuring the patient's heart rate; however, those skilled in the art realize that one could acquire the patient's heart rate from data relating to physical and medical characteristics of the patient 12. Such data could be obtained from a comprehensive database indicating an appropriate estimated heart rate for a patient 12 having certain specified physical and/or medical characteristics. Typically, the measured heart rate of interest comprises the patient's resting heart rate. The step of applying the conversion factor comprises the steps of converting the heart rate defined in beats per minute to beats per second, and multiplying the heart rate defined in beats per second by a scaling quantity. In the preferred embodiment, the scaling quantity comprises any number between approximately three and seven, inclusively; however, best results appear to occur when the scaling quantity is approximately five.

The present method further comprises the steps of calculating a first area (i.e., see horizontal shaded area 46L in FIG. 3) by integrating a selected one of the power spectrum signals from zero Hertz to the base value, calculating a second area (i.e., see solid shaded area 46H in FIG. 3) by integrating the selected one of the power spectrum signals from the base value to infinity, and dividing a first calculated value corresponding to the first area by a second calculated value corresponding to the second area to obtain an evaluation standard corresponding to the selected one of the power spectrum signals. Briefly digressing in order to help understand the context of this portion of the method, recall that the following has occurred: 1) conventional, unmodified EKG signals where amplified and digitized; 2) the amplified, digitized EKG signals are then transformed into the 12 lead signals in the time domain; 3) the 12 time domain lead signals are transformed into 12 corresponding power spectrum signals in the frequency domain, and 4) the patient's heart rate has been obtained to establish the appropriate base value.

Then, the selected power spectrum signal (i.e., one at a time is selected until all of the 12 that are desired to be analyzed have been so evaluated) is integrated from zero Hertz to the base value, which is also in units of Hertz. Similarly, one integrates the selected power spectrum signal from the base value to infinity. Here of course, an approximation short of true infinity may be implemented. Then, the first area is divided by the second area (i.e., a ratio of the first to second area) to obtain an evaluation standard corresponding to the selected power spectrum signal. Thus, each power spectrum signal has its own particular evaluation standard. In other words, since there are 12 power spectrum signals, there are 12 corresponding evaluation standards (e.g., see tables 50 and 52 of FIG. 4, each showing 6 different evaluation standard bars, albeit in repetitive form, for a total of 12 evaluation standard bars). When a selected evaluation standard comprises a value of approximately≧one, this indicates a healthy state for the patient 12, but when the selected evaluation standard comprises a value of approximately<one, this indicates an unhealthy state for the patient 12. So, if any one of the 12 evaluation standards (i.e., there is one per power spectrum signal), is approximately<one, then a patient 12 has detected heart disease. This analysis of evaluation standards comprises but one manner of detecting heart disease.

Another scheme for detecting heart disease comprises the step of analyzing peaks for each of the power spectrum signals in the frequency domain against a plurality of evaluative standards for the peaks. This detection scheme is best illustrated with respect to FIGS. 5A–5H. As with the previous manner of detecting heart disease (i.e., involving analyzing evaluation standards), the following steps have occurred: 1) conventional, unmodified EKG signals where amplified and digitized; 2) the amplified, digitized EKG signals are then transformed into 12 lead signals in the time domain; 3) the 12 time domain lead signals are transformed into 12 corresponding power spectrum signals in the frequency domain; and 4) the patient's heart rate has been obtained to establish the appropriate base value; however, the base value is not needed in peak analysis. Rather, eight different evaluative standards, which will be set forth shortly, are used in peak analysis. It should first be noted that in peak analysis, any one or more of the power spectrum signals may be analyzed under at least one, if not all eight of the peak evaluative standards, and if one or more of the power spectrum signal meets an unhealthy state for any of the peak evaluative standards, then the patient 12 has detected heart disease.

Figure 5A:
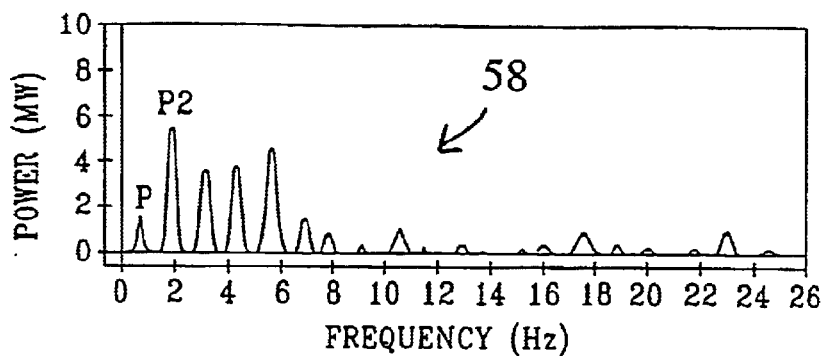
FIG. 5A is a simplified graphical depiction of one lead of a power spectrum signal in the frequency domain that shows the second peak as greater in magnitude than the first peak.

Referring to FIG. 5A, the first peak evaluative standard involves determining if the second peak is greater in magnitude than the first peak for a selected power spectrum signal as indicative of an unhealthy state for the patient 12. More specifically, FIG. 5A shows a selected power spectrum signal 58 having first P1 and second P2 peaks. The second peak P2 is greater in magnitude than the first peak P1, therefore, the patient 12 has detected heart disease. Conversely, if the second peak P2 was smaller in magnitude than the first peak P1, then the patient 12 would not have detected heart disease based on this test.

Figure 5B:
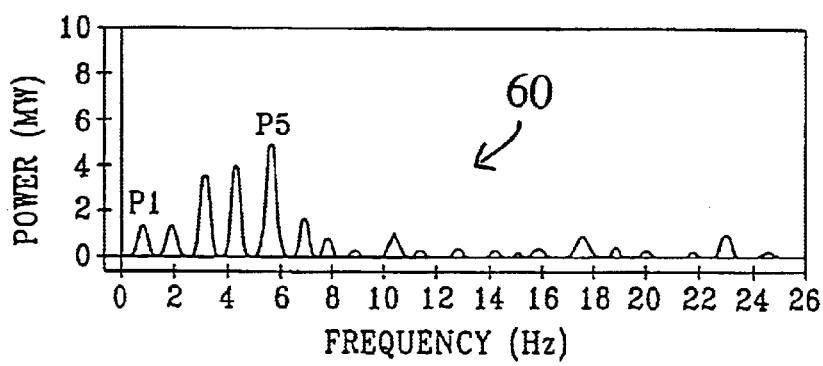
FIG. 5B is a simplified graphical depiction of one lead of a power spectrum signal in the frequency domain that shows the fifth peak as greater hi magnitude than the first peak.

Referring to FIG. 5B, the second peak evaluative standard involves determining if the fifth peak is greater in magnitude than the first peak for a selected power spectrum signal as indicative of an unhealthy state for the patient 12. More specifically, FIG. 5B shows a selected power spectrum signal 60 having first P1 and fifth P5 peaks. The fifth peak P5 is greater in magnitude than the first peak P1, therefore, the patient 12 has detected heart disease. Conversely, if the fifth peak P5 was smaller in magnitude than the first peak P1, then the patient 12 would not have detected heart disease based on this test.

Figure 5C:
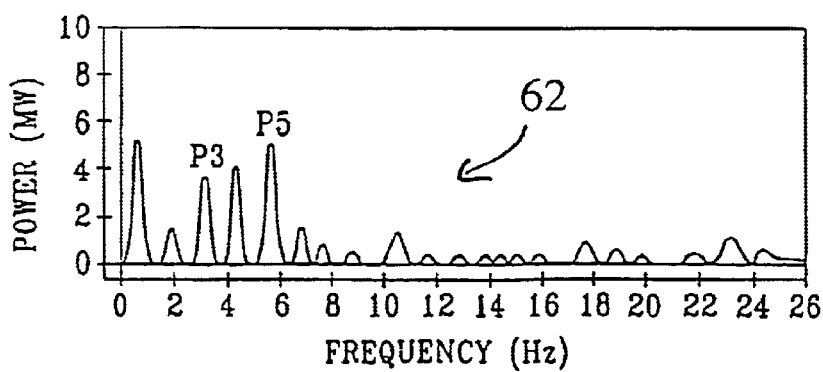
FIG. 5C is a simplified graphical depiction of one lead of a power spectrum signal in the frequency domain that shows the fifth peak as greater in magnitude than a third peak.

Referring to FIG. 5C, the third peak evaluative standard involves determining if the fifth peak is greater in magnitude than the third peak for a selected power spectrum signal as indicative of an unhealthy state for the patient 12. More specifically, FIG. 5C shows a selected power spectrum signal 62 having third P3 and fifth P5 peaks. The fifth peak P5 is greater in magnitude than the third peak P3, therefore, the patient 12 has detected heart disease. Conversely, if the fifth peak P5 was smaller in magnitude than the third peak P3, then the patient 12 would not have detected heart disease based on this test.

Figure 5D:
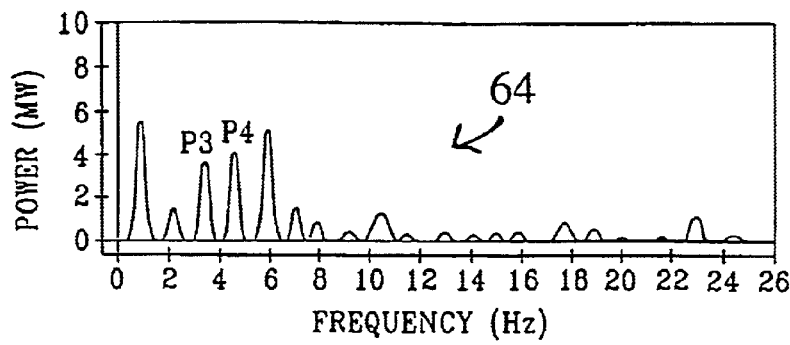
FIG. 5D is a simplified graphical depiction of one lead of a power spectrum signal in the frequency domain that shows the fourth peak as greater in magnitude than the third peak.

Referring to FIG. 5D, the fourth peak evaluative standard involves determining if the fourth peak is greater in magnitude than the third peak for a selected power spectrum signal as indicative of an unhealthy state for the patient 12. More specifically, FIG. 5D shows a selected power spectrum signal 64 having third P3 and fourth P4 peaks. The fourth peak P4 is greater in magnitude than the third peak P3, therefore, the patient 12 has detected heart disease. Conversely, if the fourth peak P4 was smaller in magnitude than the third peak P3, then the patient 12 would not have detected heart disease based on this test.

Figure 5E:
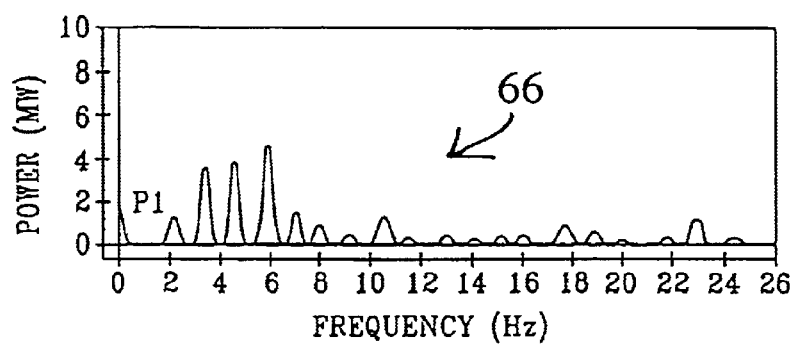
FIG. 5E is a simplified graphical depiction of one lead of a power spectrum signal in the frequency domain that shows the first peak as relatively low in magnitude.

Referring to FIG. 5E, the fifth peak evaluative standard involves determining if the first peak is relatively low in magnitude for a selected power spectrum signal as indicative of an unhealthy state for the patient 12. More specifically, FIG. 5E shows a selected power spectrum signal 66 having the first peak P1. Certainly, peak P1 would appear "relatively low in magnitude," however, a more specific standard is required here for accurate analysis. In particular, if P1<K, where K is any number between zero to 0.2 milliwatts (but preferably 0.1 milliwatts), then P1 would be considered "relatively low in magnitude." As peak P1 is not even visible, it is clear that it is less than 0.1 milliwatts. Accordingly, the patient 12 has detected heart disease. Conversely, if the first peak P1 was not "relatively low in magnitude," as that phrase has been defined, then the patient 12 would not have detected heart disease based on this test.

Figure 5F:
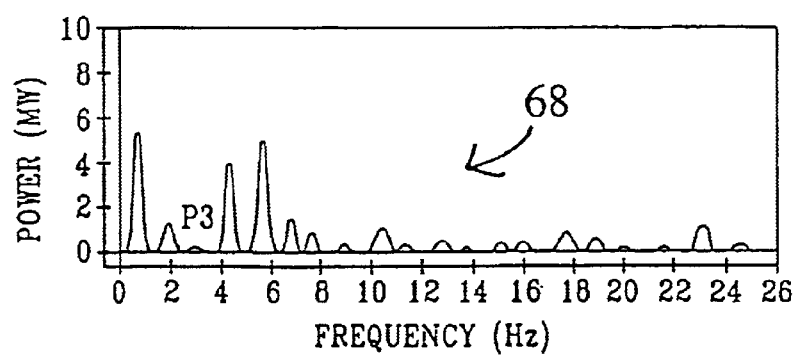
FIG. 5F is a simplified graphical depiction of one lead of a power spectrum signal in the frequency domain that shows the third peak as relatively low in magnitude.

Referring to FIG. 5F, the sixth peak evaluative standard involves determining if the third peak is relatively low in magnitude for a selected power spectrum signal as indicative of an unhealthy state for the patient 12. More specifically, FIG. 5F shows a selected power spectrum signal 68 having the third peak P3. Again, peak P3 would certainly appear "relatively low in magnitude," however, a more specific standard is required here for accurate analysis. In particular, if P3<K, where K is any number between zero to 0.2 milliwatts (but preferably 0.1 milliwatts), then P3 would be considered "relatively low in magnitude." As peak P3 is barely even visible, it would seem clear that it is less than 0.1 milliwatts. Accordingly; the patient 12 probably has detected heart disease° Conversely, if the third peak P3 was not "relatively low in magnitude," as that phrase has been defined, then the patient 12 would not have detected heart disease based on this test.

Figure 5G:
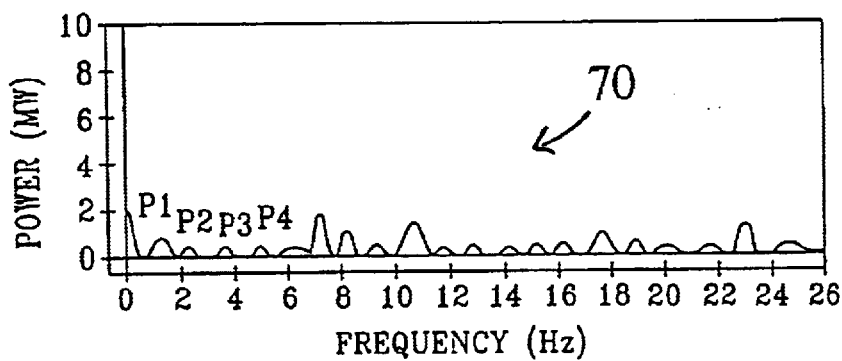
FIG. 5G is a simplified graphical depiction of one lead of a power spectrum signal in the frequency domain that slows the first, second, third, and fourth peaks as relatively low in magnitude.

Referring to FIG. 5G, the seventh peak evaluative standard involves determining if the first, second, third, and fourth peaks are relatively low in magnitude for a selected power spectrum signal as indicative of an unhealthy state for the patient 12. More specifically, FIG. 5G shows a selected power spectrum signal 70 having first P1, second P2, third P3, and fourth P4 peaks. Once again, peaks P1–P4 would certainly appear "relatively low in magnitude," however, a more specific standard is required here for accurate analysis. In particular, if (P1+P2+P3+P4)<K, where K is any number between zero to 8 milliwatts (but preferably 4 milliwatts), then P1–P4 would be considered "relatively low in magnitude." As the sum of peaks P1–P4 appears less than 4 milliwatts, the patient 12 probably has detected heart disease. Conversely, if the sum of peaks P1–P4 was not "relatively low in magnitude," as that phrase has been defined, then the patient 12 would not have detected heart disease based on this test.

Figure 5H:
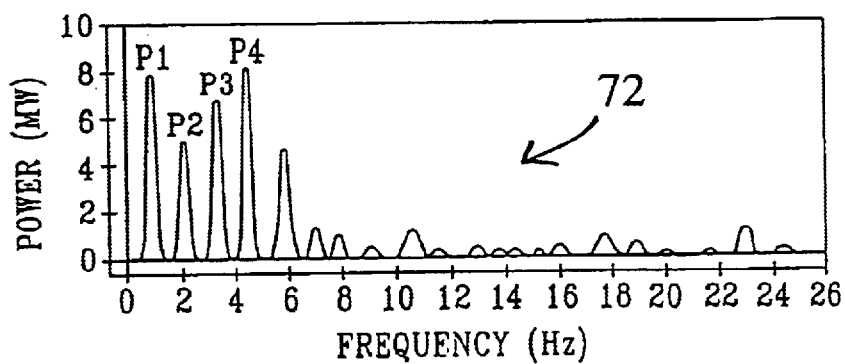
FIG. 5H is a simplified graphical depiction of one lead of a power spectrum signal in the frequency domain that shows the first, second, third, and fourth peaks as relatively high in magnitude.

Referring to FIG. 5H, the eighth peak evaluative standard involves determining if the first, second, third, and fourth peaks are relatively high in magnitude for a selected power spectrum signal as indicative of an unhealthy state for the patient 12. More specifically, FIG. 5H shows a selected power spectrum signal 72 having first P1, second P2, third P3, and fourth P4 peaks. Once more, peaks P1–P4 would certainly appear "relatively high in magnitude," however, a more specific standard is required here for accurate analysis. In particular, if $(P1+P2+P3+P4) \geq K$, where K is any number between 20–40 milliwatts (but preferably 30 milliwatts), then P1–P4 would be considered "relatively high in magnitude." Peaks P1–P4 appear to have approximate magnitudes of 8 milliwatts, 5 milliwatts, 7 milliwatts, and 8.5 milliwatts, respectively. Accordingly, their sum is 28.5 milliwatts, which depending upon the analytical value (within 20–40 milliwatts) chosen for K, may or may not indicate detected heart disease. Note however that if the sum of peaks P1–P4 was clearly not "relatively high in magnitude," as that phrase has been defined, then the patient 12 would not have detected heart disease based on this test.

The present method not only has the capability to detect heart disease (as substantially covered above) but it also has the ability to locate the source or sources heart disease. The locating methodology comprises the steps of providing a plurality of locating standards wherein each locating standard corresponds to a distinct location of potential heart disease, and evaluating each locating standard of the plurality of locating standards to determine whether any distinct locations have heart disease. The step of providing a plurality of locating standards comprises the step of establishing a sum of different evaluation standards for each locating standard of the plurality of locating standards. In other words, there are a plurality of locating standards, and each is equal to a different combination of evaluation Standards. The evaluation standards are computed as previously discussed, namely by taking the ratio of the lower frequency area (e.g., 46L in FIG. 3) to the higher frequency area (e.g., 46H in FIG. 3) for a selected power spectrum signal.

The step of evaluating each locating standard comprises the steps, repeated for each locating standard, of adding the sum of different evaluation standards for a selected locating standard, comparing the sum to the number of evaluation standards comprising the sum for the selected locating standard to determine whether the sum is ≧ the number of evaluation standards, and to determine whether the sum is < the number of evaluation standards, assigning the distinct location of potential heart disease corresponding to the selected locating standard with a determination of an unhealthy state for the patient 12 when the sum is < the number of evaluation standards, and assigning the distinct location of potential heart disease corresponding to the selected locating standard with a determination of a healthy state for the patient 12 when the sum is ≧ the number of evaluation standards.

The plurality of locating standards and their corresponding distinct locations of potential heart disease define the following analysis table:

| LOCATING STANDARDS | | LOCATIONS OF POTENTIAL HEART DISEASE: |
|---|---|---|
| (1) V1 + V2 + V3 + V4 | ←→ | Anteroseptal |
| (2) V2 + V3 + V4 + V5 | ←→ | Anterior |
| (3) II + aVF + VI + V2 | ←→ | Inferior Posterior |
| (4) I + aVL + V3 + V4 + V5 + V6 | ←→ | Anterolateral |
| (5) I + aVL + V5 + V6 | ←→ | Lateral |
| (6) I + aVR + aVL + V6 | ←→ | Lead I Area |
| (7) II + aVR + aVF | ←→ | Lead II Area |
| (8) III + aVL + aVF | ←→ | Lead III Area |
| (9) I + II + aVR + V5 | ←→ | Lead aVR Area |
| (10) I + III + aVL | ←→ | Lead aVL Area |
| (11) II + III + aVF | ←→ | Lead aVF Area |
| (12) V1 + V2 + V6 | ←→ | Lead V1 Area |
| (13) V1 + V2 + V3 | ←→ | Lead V2 Area |
| (14) V2 + V3 + V4 | ←→ | Lead V3 Area |
| (15) V3 + V4 + V5 | ←→ | Lead V4 Area |
| (16) V4 + V5 + V6 | ←→ | Lead V5 Area |
| (17) V1 + V5 + V6 | ←→ | Lead V6 Area |
| (18) V1 + V2 | ←→ | Septal |
| (19) II + aVF | ←→ | Inferior |

The example provided hereafter is perhaps the best way to understand the usefulness of the locating method outlined above. Initially, note the form of the first entry, which reads, "(1) V1+V2+V3+V4≦Anteroseptal." Here, the number (1) indicates that this is the first of 19 entries in the analysis table. Next, note that V1, V2, V3, and V4 are each evaluation standards, and this unique combination of evaluation standards equates to the first locating standard of 19 different location standards. In other words, each of the 19 different locating standards corresponds to a different combination of evaluation standards. Next, the four evaluation standards V1–V4 are computed to obtain four numerical values corresponding to the four evaluation standards V1–V4, as previously described. Then, those four values are added to obtain a sum of the four computed evaluation standards V1–V4. The computed sum is compared to the number of evaluation standards defining the selected locating standard, in this case, four. If the sum of computed evaluation standards is less than four, then the patient 12 has detected heart disease at the corresponding distinct location; however, if the sum of computed evaluation standards is ≧ four, then there is no detected heart disease at the corresponding distinct location. Here, for entry (1) in the analysis table, that location is the Anteroseptal region of the heart. Those skilled in the art understand the location of the heart corresponding to the Anteroseptal region, as well as the other 18 location entries in the analysis table. Each of the other 18 entries in the analysis table would be handled in the same manner as described above to determine potential locations of heart disease. Thus, one would use one of the previously discussed manners to determine if a patient 12 has detected heart disease, and if so, then the analysis immediately above in connection with the analysis table would be used to locate the source or sources of heart disease. Lastly, it should be pointed out that the order of entries from top to bottom in the analysis table is of significance, as will be pointed out below.

When the sum is ≧ its corresponding number of evaluation standards for each locating standard of the plurality of locating standards, no distinct location of potential heart disease is detected. When the sum is < its corresponding number of evaluation standards for only one locating standard of the plurality of locating standards, the distinct location corresponding to that one locating standard has detected heart disease. On the other hand, when the sum is < its corresponding number of evaluation standards for more than one locating standard of the plurality of locating standards, each distinct location corresponding to those locating standards has detected heart disease. When a plurality of locating standards have their sums < their corresponding number of evaluation standards, a prioritization scheme for most accurately locating the source or sources of heart disease is set up by the order in which the 19 entries fall from top to bottom in the analysis table. In particular, when a plurality of locating standards have their sums < their corresponding number of evaluation standards, the upper most locating standard in the analysis table of those locating standards with their sums < their corresponding number of evaluation standards identifies the corresponding distinct location of potential heart disease with the most accuracy. The accuracy in fully and completely identifying the distinct locations of potential heart disease for a patient 12 descends as one moves down the analysis table focusing on the remaining locating standards with their sums < their corresponding number of evaluation standards. For example, if the locating standards corresponding to entries (1), (4) and (8) in the analysis table had their sums < their corresponding number of evaluation standards, then a listing of distinct potential locations for detected heart disease of descending accuracy would be: (1) Anteroseptal, (4) Anterolateral, and (8) Lead III Area.

As a point of general interest to the present method for detecting and locating heart disease, note that all of the 12 lead signals are simultaneously and continuously obtained over a period of time for the step of converting the altered signals in the time domain into power spectrum signals in the frequency domain. This period of time comprises a duration in excess of one second, and preferably a duration of approximately 88 seconds.

As an alternative embodiment of the present invention, a system 10 (see FIG. 1A) for detecting and locating heart disease comprises, in combination, a portion for obtaining electrocardiograph (EKG) signals from a patient 12, a portion for modifying the EKG signals coupled to the portion for obtaining, and a portion for establishing a base value for use in evaluating modified EKG signals. The portion for obtaining electrocardiograph (EKG) signals from a patient 12 includes an electrocardiograph (not shown), its connectors (also not shown) to the patient 12, and any other equipment generally used in the operation of an electrocardiograph. The portion for modifying tile EKG signals includes the amplification logical block 14, the A/D conversion logical block 16, and the computer 17, which has an operating system and means for performing the various computations discussed above. In the preferred embodiment, the computer's operating system comprises a windows-based operating system, such as WINDOW 95. However, those skilled in the art will recognize that any well known operating system could be implemented, if desired.

As for the means for performing the various computations discussed above, this implies computer functionality. Such functionality includes: 1) taking amplified, digitized EKG signals and transforming them into 12 lead signals in the time domain, as previously discussed; 2) taking the 12 lead signals in the time domain and transforming them into 12 power spectrum signals in the frequency domain, as previously discussed; 3) taking, the heart rate measured in beats per minute, converting it to beats per second, and applying the scaling factor to obtain the base value, as previously discussed; 4) integrating the 12 power spectrum signals to obtain the areas from which the 12 evaluation standards are computed, as previously discussed; 5) conducting peak analysis, as discussed above; 6) adding the various combinations of evaluation standards comprising the locating standards, as previously discussed; and 7) comparing the evaluation standard sums to their corresponding number of evaluation standards to determine potential locations of heart disease, also as previously discussed. Those skilled in the art realize that the above-identified functionalities, and any others inherent in the operation of the present invention 10, involve such well known and straight forward processes as adding, subtracting, multiplying, dividing, integrating, and Fourier transformation. Accordingly, those skilled in the art understand that any one of a plurality of different and well known processes may be implemented to accomplish the above-identified functionalities As to the portion for establishing a base value for use in evaluating modified EKG signals, this involves measuring the patient's heart rate in beats per minute, converting it to beats per second, and then applying the scaling quantity to obtain the base value for use by the computer 17. Alternatively, the patient's heart rate in beats per minute may be obtained from a database, as previously mentioned, and then modified as discussed above for the measured heart rate scenario.

Although the invention has been particularly shown and described with reference to a preferred embodiment thereof, it will be understood by those skilled in the art that changes in form and detail may be made therein without departing from the spirit and scope of the invention. For example, the present methodology and system have been defined as for use in detecting and locating heart disease; however, the general phrase, "heart disease" is intended to include, but is not necessarily limited to the detection and potential location of a source or sources of myocardial ischaemia and infarction.

What is claimed is:

1. A system for detecting and locating heart disease comprising, in combination:
   an electrocardiograph for receiving electrical signals from a patient's heart;
   an electrocardiograph signal modifier coupled to said electrocardiograph for creating modified signals from said electrical signals;
   a base value calculator for calculating a base value; and
   a computer to calculate an evaluation standard using the base value and the modified signals and to calculate a location standard using the evaluation standard.

2. The system of claim 1 wherein said base value calculator comprises a heart rate measurer to measure a patient's heart rate, and a heart rate converter said heart rate converter applying a conversion factor to said heart rate producing said base value.

3. The system of claim 2 wherein said heart rate converter converts said heart rate from beats per minute into beats per second; and
   a heart rate multiplier multiplies said heart rate, as measured in beats per second, by a scaling quantity.

4. The system of claim 3 wherein said scaling quantity comprises any number between approximately three and seven, inclusively.

5. The system of claim 3 wherein said scaling quantity preferably comprises a number five.

6. A system for detecting and locating heart disease comprising, in combination:
   an electrocardiograph for receiving electrical signals from a patient's heart;
   an electrocardiograph signal modifier coupled to said electrocardiograph for creating modified signals from said electrical signals;
   a base value calculator for calculating a base value;
   wherein said electrocardiograph signal modifier further includes:
      an amplifier, for amplifying said electrical signals;
      an A/D converter, for digitizing said amplified electrical signals; and
      a processor coupled to said A/D converter;
         wherein said processor mathematically modifies said amplified and digitized electrical signals to obtain altered signals in time domain;
         wherein said processor converts said altered signals in said time domain into power spectrum signals in a frequency domain;
         wherein said processor calculates a first area by integrating a selected one of said power spectrum signals from zero Hertz to said base value;
         wherein said processor calculates a second area by integrating said selected one of said power spectrum signals from said base value to infinity; and
         wherein said processor divides a first calculated value corresponding to said first area by a second calculated value corresponding to said second area to obtain an evaluation standard corresponding to said selected one of said power spectrum signals;

a computer detecting heart disease by comparing the valuation standard to one; and said computer locating heart disease by computing a location standard using the evaluation standard.

7. The system of claim 6 wherein a value of approximately≧one for said evaluation standard indicates a healthy state for said patent, and a value of approximately<one for said evaluation standard indicates an unhealthy state for said patient.

* * * * *